United States Patent
Tanaka et al.

(10) Patent No.: US 9,528,937 B2
(45) Date of Patent: Dec. 27, 2016

(54) CLINICAL EXAMINATION APPARATUS AND METHOD

(75) Inventors: Yousuke Tanaka, Kobe (JP); Takamichi Naito, Kobe (JP); Toru Mizumoto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1688 days.

(21) Appl. No.: 11/729,661

(22) Filed: Mar. 29, 2007

(65) Prior Publication Data
US 2007/0233518 A1    Oct. 4, 2007

(30) Foreign Application Priority Data

Mar. 30, 2006 (JP) ................................. 2006-094496

(51) Int. Cl.
| | | |
|---|---|---|
| *G01N 31/00* | (2006.01) | |
| *G01N 33/48* | (2006.01) | |
| *G01N 21/64* | (2006.01) | |
| *G01N 35/00* | (2006.01) | |
| *G06Q 50/22* | (2012.01) | |
| *G06F 19/00* | (2011.01) | |

(52) U.S. Cl.
CPC ........ *G01N 21/64* (2013.01); *G01N 35/00594* (2013.01); *G06Q 50/22* (2013.01); *G06F 19/366* (2013.01)

(58) Field of Classification Search
None
See application file for complete search history.

(56) References Cited

U.S. PATENT DOCUMENTS

| | | | | |
|---|---|---|---|---|
| 6,183,697 | B1 * | 2/2001 | Tanaka et al. | 422/82.05 |
| 2001/0039053 | A1 * | 11/2001 | Liseo | G01N 35/10 |
| | | | | 436/43 |
| 2004/0122708 | A1 * | 6/2004 | Avinash et al. | 705/2 |
| 2005/0102166 | A1 * | 5/2005 | Tohma | 705/3 |
| 2006/0064324 | A1 * | 3/2006 | Rosenfeld et al. | 705/2 |

FOREIGN PATENT DOCUMENTS

| | | | |
|---|---|---|---|
| JP | 05-151282 | 6/1993 | |
| JP | 11-45302 | 2/1999 | ............. G06F 19/00 |
| JP | 2002-22748 | 1/2002 | ............. G01N 35/00 |

* cited by examiner

*Primary Examiner* — Anna Skibinsky
(74) *Attorney, Agent, or Firm* — Brinks Gilson & Lione

(57) ABSTRACT

A clinical examination apparatus is equipped with a measurement unit which measures a patient's clinical specimen, an output unit which outputs the measurement result by this measurement unit and a storage unit which stores determination criteria of the measurement result by the measurement unit according to a medical organization. Moreover, the clinical examination apparatus determines whether or not the measurement result corresponds to a predetermined state based on the measurement result by the measurement unit and the determination criteria stored in the storage unit, for each medical organization, and upon determination that the measurement result corresponds to a predetermined state, allows the output unit to output information indicating the predetermined state.

13 Claims, 12 Drawing Sheets

CLINICAL EXAMINATION APPARATUS AND METHOD

RELATED APPLICATIONS

This application claims priority under 35 U.S.C. §119 to Japanese Patent Application No. 2006-094496 filed Mar. 30, 2006, the entire content of which is hereby incorporated by reference.

FIELD OF INVENTION

This invention relates to a clinical examination apparatus.

BACKGROUND

Conventionally, various kinds of clinical examination apparatuses are designed to compare a test result with a predetermined range of normal values so that upon determination that the test result is abnormal, information indicating the abnormality is outputted.

Japanese Patent Laid-Open No. 5-151282 has disclosed a clinical examination apparatus in which, after normal value ranges for respective examination items have been registered according to the gender and the age range, a determining process for any abnormal value is carried out based upon determination conditions that match classifications of the gender and the age range, in accordance with information of a patent's data.

However, depending on examination items, the handling of a test result tends to change with a specialty of medical field (a department in a hospital), ward, etc., and, in such a case, the determination criteria of a test result are different depending on the respective specialties, wards, etc. For example, in the case of the determination criteria for UTI (urinary tract infection), in general, the test result is determined as UTI when the bacteria concentration in urine is $10^4$ or more pieces/ml; however, in the case of pediatrics, the determination criteria are made severer so that it is determined as UTI in the case of $10^3$ or more pieces/ml, while in the case of obstetrics and gynecology, the determination criteria are made loose so that it is determined as UTI in the case of $10^5$ or more pieces/ml.

In other words, even if a test result is determined simply based upon determination criteria classified only for the physical information of a patient to receive a medical examination, such as the gender, the age range, etc., as has been conventionally carried out, the determination tends to fail to satisfy the individual demand of a doctor, etc. who carries out a medical examination in each specialty, ward or the like, and in such a case, the doctor or the like has to again conduct a determining process in accordance with determination criteria prepared according to each of the specialty, the ward and the like.

BRIEF SUMMARY

The scope of the present invention is defined solely by the appended claims, and is not affected to any degree by the statements within this summary.

A first aspect of the present invention is a clinical examination apparatus comprising:

measurement means for measuring a clinical specimen extracted from a patient;

a storage unit for storing a first determination criterion and a second determination criterion used for classifying the measurement result obtained by the measurement means, the first determination criterion corresponding to a first medical organization and the second determination criterion corresponding to a second medical organization;

first determination means for determining whether or not the measurement result is in a first state for the first medical organization, based upon the first determination criterion stored in the storage unit;

second determination means for determining whether or not the measurement result is in a second state for the second medical organization, based upon the second determination criterion stored in the storage unit;

a display unit;

first displaying means for displaying first information indicating the measurement result being in the first state on the display unit, when the first determination means determines that the measurement result is in the first state; and second displaying means for displaying second information indicating the measurement result being in the second state on the display unit, when the second determination means determines that the measurement result is in the second state.

A second aspect of the present invention is a clinical examination apparatus comprising:

measurement means for measuring a clinical specimen extracted from a patient;

a display unit;

displaying means for displaying the measurement result obtained by the measurement means on the display unit;

a storage unit for storing a first determination criterion and a second determination criterion used for classifying the measurement result obtained by the measurement means, the first determination criterion corresponding to a first medical organization and the second determination criterion corresponding to a second medical organization;

receiving means for receiving a medical organization information used for identifying a medical organization related to the patient;

first determination means for determining whether or not the measurement result is in a first state based upon the first determination criterion, when the first medical organization is identified by the medical organization information received by the receiving means; and second determination means for determining whether or not the measurement result is in a second state based upon the second determination criterion, when the second medical organization is identified by the medical organization information received by the receiving means, wherein the displaying means displays first information indicating that the measurement result is in the first state when the first determination means determines the measurement result is in the first state, and displays second information indicating that the measurement result is in the second state when the second determination means determines the measurement result is in the second state.

A third aspect of the present invention is a clinical examination method comprising:

measuring a clinical specimen extracted from a patient;

comparing the measurement result with a first determination criterion which corresponds to a first medical organization and determining whether or not the measurement result is in a first state;

comparing the measurement result with a second determination criterion which corresponds to a second medical organization and determining whether or not the measurement result is in a second state;

displaying first information indicating the measurement result being in the first state on a display unit, when the measurement result is in the first state; and displaying second information indicating the measurement result being in the second state on the display unit, when the measurement result is in the second state.

DETAILED DESCRIPTION OF THE PREFERRED EMBODIMENTS

Referring to Figures, the following description will discuss embodiments of the clinical examination apparatus in accordance with this invention.

Figure 1:
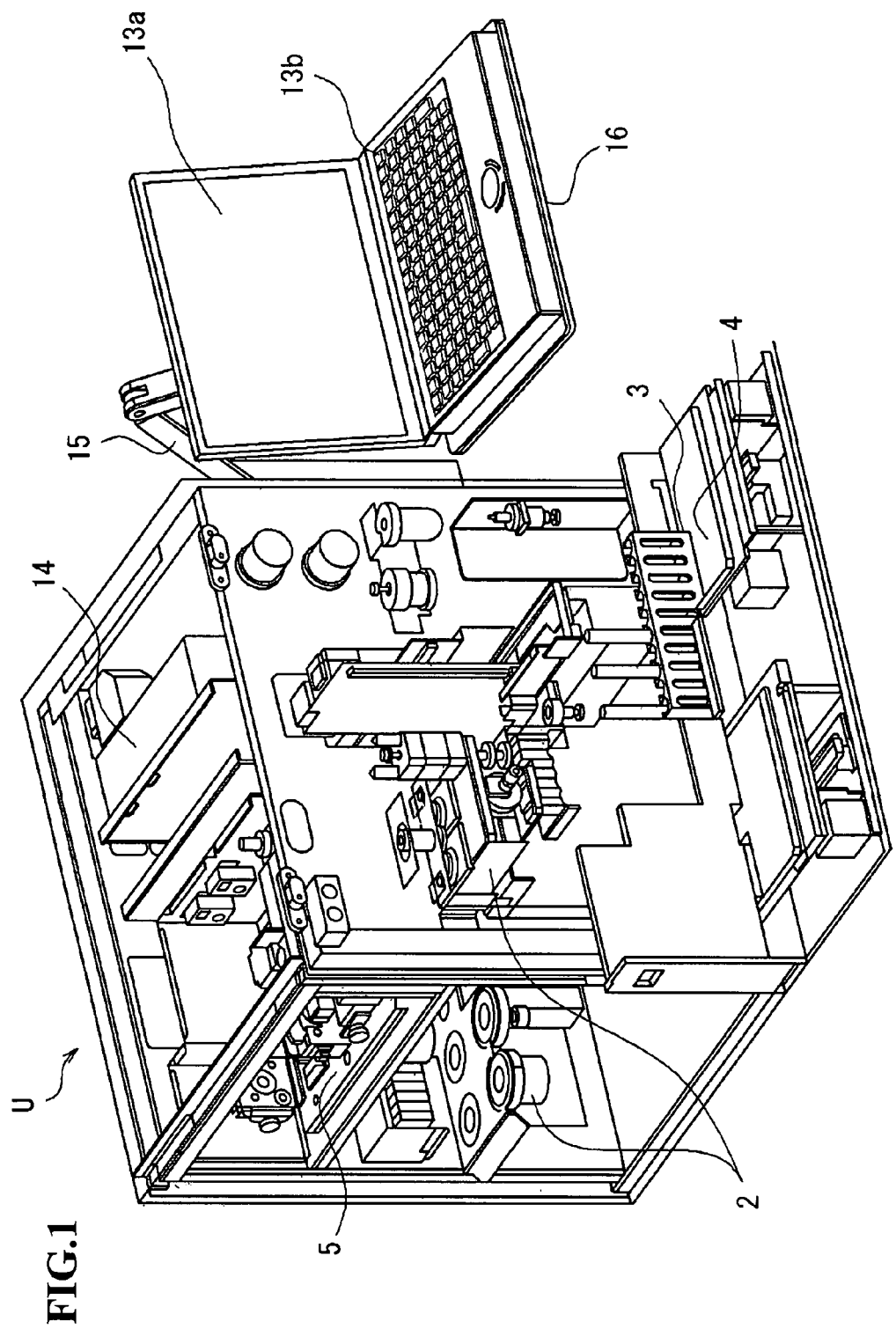
FIG. 1 is a perspective explanatory drawing that shows a urine analyzer in accordance with one embodiment of a clinical examination apparatus.

FIG. 1 is a perspective explanatory drawing of the clinical examination apparatus in accordance with one embodiment of the present invention. In FIG. 1, to help understanding, the chassis used for accommodating the constituent elements of the clinical examination apparatus is omitted partially.

[Configuration of Apparatus]

In FIG. 1, the urine analyzer U which serves as a clinical examination apparatus is equipped with a sample preparation unit 2 for preparing a sample, a rack table 4 which transports a sample rack (test-tube stand) 3, an optical detecting unit 5 used for detecting the information on particle ingredient (sediments) or bacteria in urine from a sample and a circuit unit 14. A support stand 16 is attached to the chassis side face through an arm 15, and a personal computer 13 is installed thereon. The personal computer 13 is LAN-connected to the circuit unit 14 of the urine analyzer U.

In the present embodiment, the measuring unit used for measuring a patient's clinical specimen is mainly constituted by the optical detecting unit 5 and the circuit unit 14, and the output unit used for outputting a measurement result by the measuring unit is constituted by a display 13a of the personal computer 13. Moreover, the personal computer 13 is provided with a storage unit that stores the criterion on the measurement results by the measurement unit according to medical organizations, such as a specialty, a clinic, a hospital and a ward, independently. The personal computer 13 is further provided with a determination means that determines whether the measurement result in question belongs a predetermined state for every medical organization based upon the result of measurements by the measurement unit and the determination criteria stored in the storage means, and a CPU 104a which, upon determination by the determination means that the above-mentioned measurement result belongs to any predetermined state, functions as an output means used for outputting information indicating the predetermined state onto the display 13a. The personal computer 13, which is connected to a host computer, for example, in a hospital, is allowed to acquire patient information about the patient in question, such as a name, birth date (age), and a specialty that the patient is consulting, from the corresponding host computer.

Figure 2:
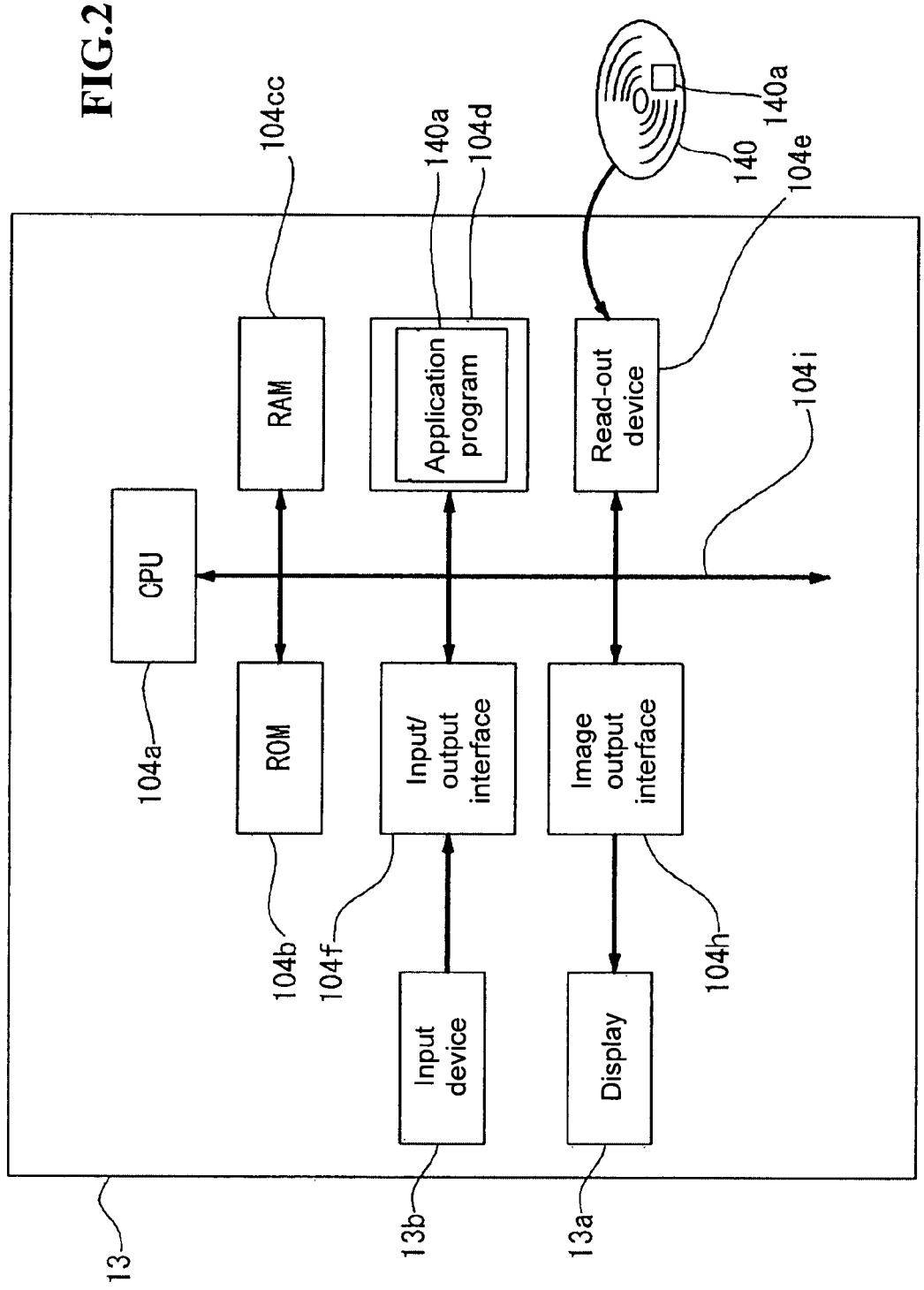
FIG. 2 is a block diagram showing a hardware configuration of a personal computer shown in FIG. 1.

More specifically, the above-mentioned personal computer 13 is equipped with the following devices. As shown in FIG. 2, the personal computers 13 has the CPU 104a, a ROM 104b, a RAM 104c, a hard disk 104d, and a read-out device 104e, an input/output interface 104f, a communication interface 104g and an image output interface 104h, and these CPU 104a, ROM 104b, RAM 104c, hard disk 104d, read-out apparatus 104e, input/output interface 104f and image output interface 104h are connected to one another by a bus 104i so as to allow data communications.

The CPU 104a can execute computer programs stored in the ROM 104b and computer programs loaded to the RAM 104c. When the CPU 104a executes an application program 140a which will be described later, the personal computer 13 is allowed to function as a system.

The ROM 104b is constituted by a mask ROM, a PROM, an EPROM, an EEPROM, etc., and the computer programs to be executed by the CPU 104a and the data used for the computer programs are recorded in this device.

The RAM 4c is constituted by a SRAM or a DRAM, etc. The RAM 4c is used for reading out the computer programs recorded on the ROM 4b and the hard disk 4d. Moreover, upon executing these computer programs, it is used as work area of the CPU 4a.

Various computer programs to be executed by the CPU 104a, such as an operating system and an application program, and data used for executing the computer programs are installed in the hard disk 104d. The application program 140a to be described later is also installed in the hard disk 104d.

The read-out device 104e is constituted by a flexible disk drive, a CD-ROM drive, or a DVD-ROM drive, and can read a computer program or data recorded on a portable type recording medium 140. Moreover, the application program 140a for operating a personal computer 13 as a system of this invention is stored in the portable type recording medium 140, and the personal computer 13 is allowed to read out the application program 140a relating to the present invention from the portable type recording medium 140, and to install the application program 140a on the hard disk 104d Here, the application program 140a is not only prepared by the portable type recording medium 140, but also prepared by an external apparatus that is communicatably connected to the personal computer 13 through electric communication line (regardless of a cable or radio) by the electric communication line. For example, the above-mentioned application program 140a is stored in the hard disk of a server computer on the Internet, and the personal computer 13 accesses this server computer to download the computer program so that the computer program may be installed on a hard disk 104d.

Moreover, an operating system which offers a graphical user interface environment, such as Windows (®) manufactured and sold by U.S. Microsoft Corp., is installed on the hard disk 104d. In the following explanation, the application program 140a relating to the present embodiment is allowed to operate on the corresponding operating system.

The input/output interface 104f is formed by, for example, a serial interface, such as a USB, an IEEE1394 and an RS-232C, a parallel interface such as an SCSI, an IDE and an IEEE1284, and an analog interface, such as a D/A converter and an A/D converter. An input device (input means) 13b, which consists of a keyboard, a mouse, etc., is connected to the input/output interface 104f, and by using the input device 13b, the user is allowed to input data into the personal computer 13. The image output interface 104h, which is connected to the display 13a constituted by a LCD or CRT, outputs an image signal corresponding to the image data given from the CPU 104a to the display 13a. The display 13a displays a picture (screen) according to the inputted image signal.

Figure 3:
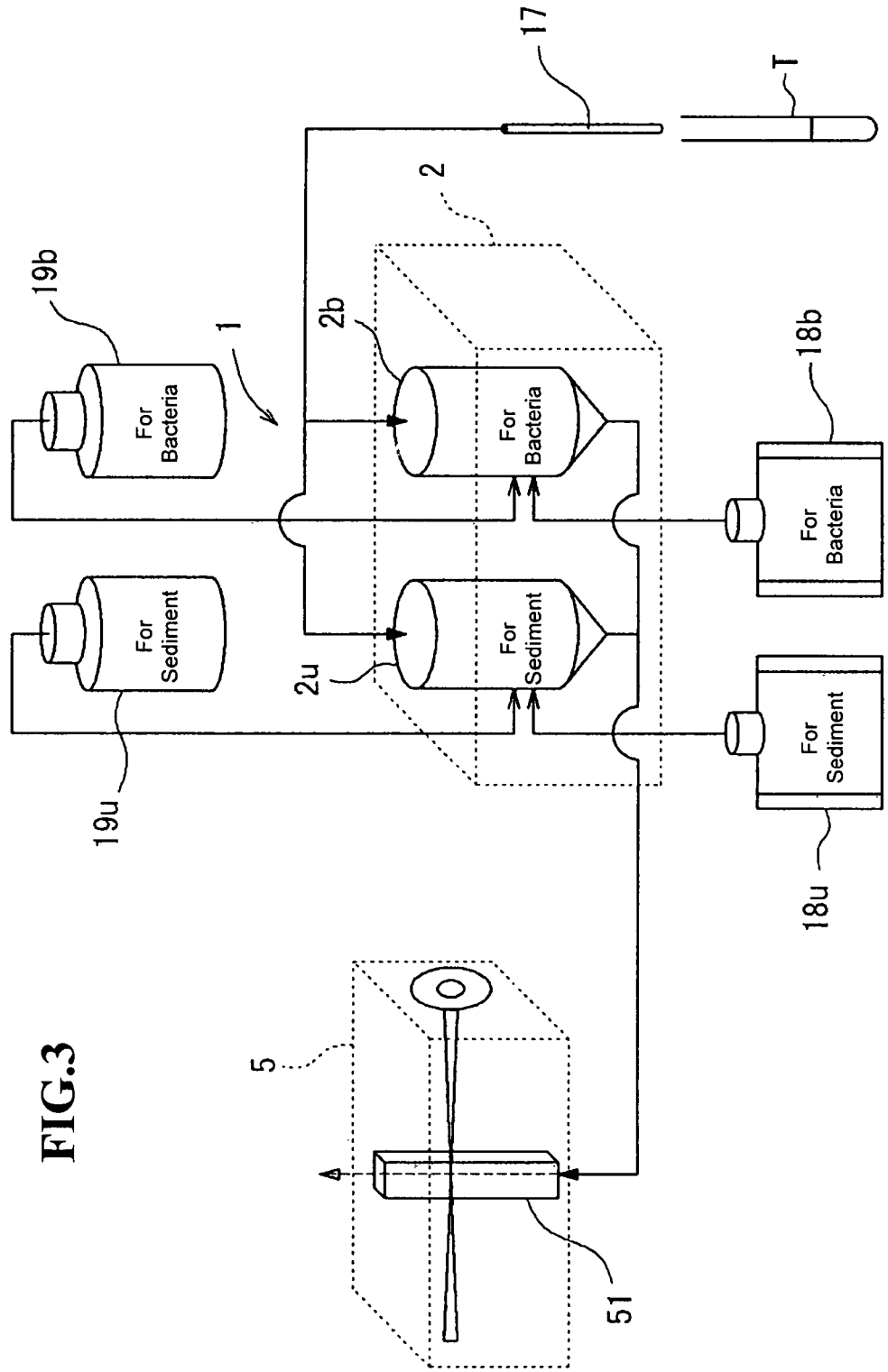
FIG. 3 is a drawing that shows a schematic functional configuration of a sample preparation unit and an optical detecting unit of the urine analyzer.

FIG. 3 is a drawing that shows schematic functional configurations of the sample preparation unit 2 and the optical detecting unit 5. In this Figure, urine (sample) included in a test tube T is attracted by a syringe pump, not shown, through a suction pipe 17, and is distributed to the sample preparation units by a sample distribution unit 1. In the present embodiment, the sample preparation units include a sample preparation unit (first sample preparation unit) 2u and a sample preparation unit (second sample preparation unit) 2b, and the sample preparation unit 2u accommodates a crust-based aliquot (1st aliquot) used for analyzing comparatively large particle ingredients in urine, such as red corpuscles, white corpuscles, epithelial cells and columnar cells, and in contrast, the sample preparation unit 2b accommodates a bacteria-based aliquot (2nd aliquot) used for analyzing comparatively small particle ingredients like bacteria.

The urine of each of the sample preparation units 2u and 2b is diluted by each of the diluted solutions 19u and 19b, and stain solutions (dyeing reagents) 18u and 18b are then mixed therein so that dyeing processes are performed respectively with coloring matters contained in the stain solutions (dyeing reagents) 18u and 18b; thus, suspensions having particle ingredients are prepared. A first sample to be used for measuring particle ingredients containing at least red corpuscles in urine is prepared by the sample preparation unit 2u, and a second sample to be used for measuring bacteria is prepared by the sample preparation unit 2b.

With respect to the two kinds of suspensions (samples) thus prepared, the suspension (the first sample) of the sample preparation unit 2u is first led to the optical detecting unit 5, and is formed into a thin flow covered with a sheath solution in the sheath flow cell 51, and this is subjected to irradiation with a laser beam. Thereafter, similarly, the suspension (the second sample) of the sample preparation unit 2b is led to the optical detecting unit 5, and is formed into a thin flow in the sheath flow cell 51, and this is subjected to irradiation with a laser beam. Such operations are automatically performed by operating an actuator, an electromagnetic valve, etc., not shown, through control of the microcomputer 11 (control device), which will be described later.

Figure 4:
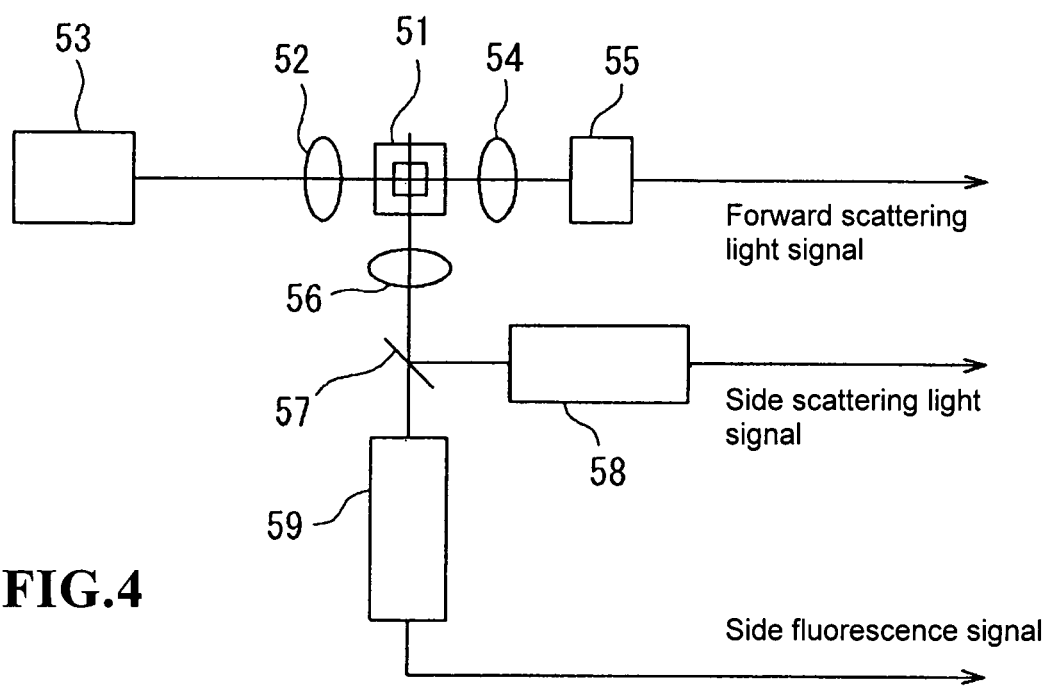
FIG. 4 is a drawing that shows a configuration of the optical detecting unit.

FIG. 4 is a drawing that shows the configuration the optical detecting unit 5. In this Figure, a condenser lens 52 condenses laser light rays emitted from a semiconductor laser 53 serving as a light source to the sheath flow cell 51, and a condenser 54 condenses forward scattering light rays of the particle ingredients in urine to a photo-diode 55 which serves as a scattering light receiving unit. Moreover, other condensers 56 condense side scattering light rays and side fluorescence of the above-mentioned particle ingredients to a dichroic mirror 57. The dichroic mirror 57 reflects the side scattering light rays to a photo-multiplier 58 which serves as a scattering light receiving unit, and the side fluorescence is made to penetrate toward a photo-multiplier 59 serving as a fluorescence receiving unit. These light signals are allowed to reflect features of the particle ingredients in urine. Moreover, the photo-diode 55, the photo-multiplier 58 and the photo-multiplier 59 convert a light signal into an electric signal, and output a forward scattering light signal (FSC), a side scatting light signal (SSC) and a side fluorescence signal (SFL), respectively. These outputs are amplified by a preamplifier, not shown, and then subjected to processes in the following steps.

Figure 5:
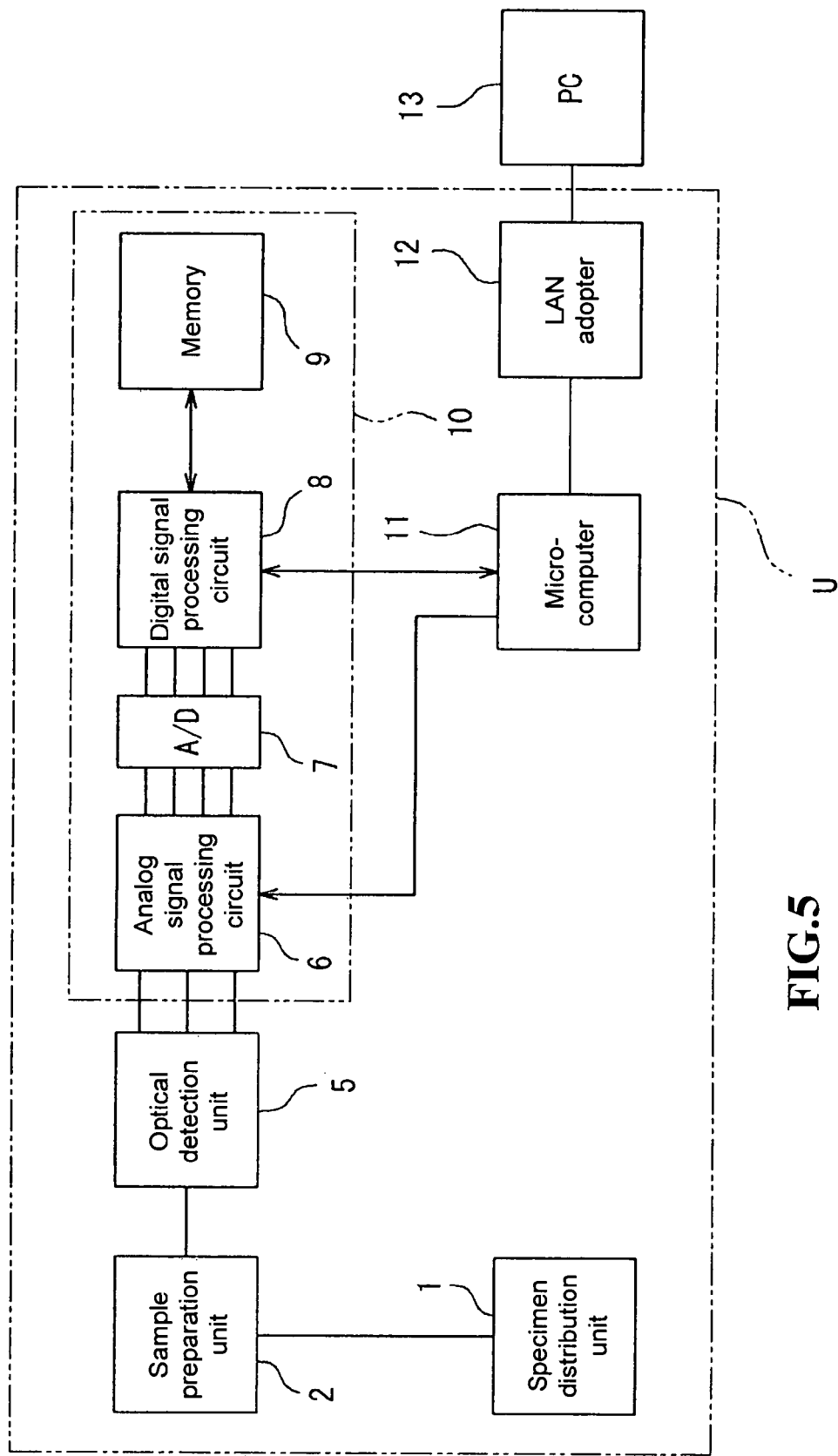
FIG. 5 is a block diagram showing the entire configuration of the urine analyzer shown in FIG. 1.

FIG. 5 is a block diagram showing the entire configuration of the urine analyzer U. In this Figure, the urine analyzer U is constituted by the aforementioned sample distribution unit 1, sample preparation unit 2 and optical detecting unit 5, an analog signal processing circuit 6 which performs an amplifying process, a filtering process and the like on a signal derived from an output of the optical detecting unit 5, which has been amplified by a preamplifier, an A/D converter 7 which converts the output of the analog signal processing circuit 6 into a digital signal, a digital signal-processing circuit 8 which carries out predetermined waveform processing on the digital signal, a memory 9 connected to the digital signal-processing circuit 8, a microcomputer 11 connected to the analog signal processing circuit 6 and the digital signal-processing circuit 8, and a LAN adapter 12 connected to the microcomputer 11. The personal computer 13 is LAN-connected to the urine analyzer U through this LAN adapter 12, and analysis of the data acquired from the urine analyzer U is conducted by the personal computer 13. The above-mentioned analog signal processing circuit 6, A/D converter 7, digital signal-processing circuit 8 and memory 9 constitute a signal-processing circuit 10 used for electric signals outputted from the optical detecting unit 5.

Figure 6:
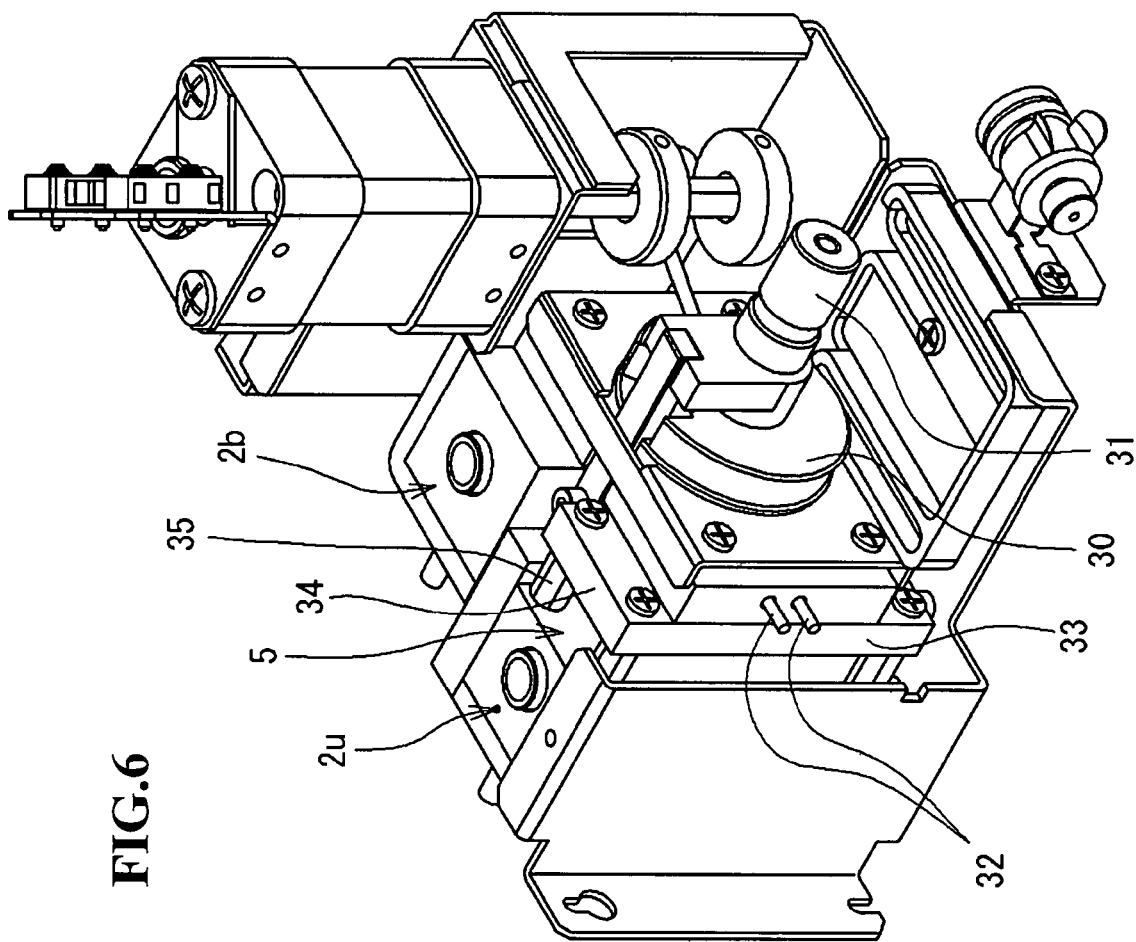
FIG. 6 is a schematic perspective view showing a quantity-measuring mechanism and a sample preparation unit of the urine analyzer.
Figure 7:
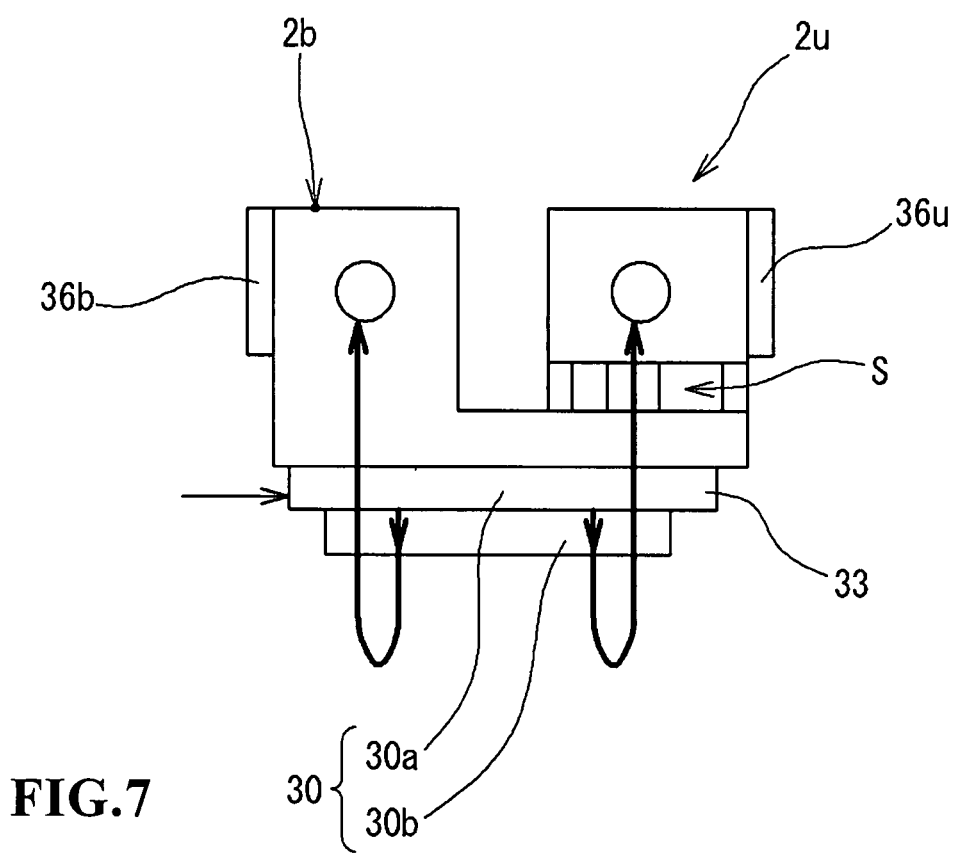
FIG. 7 is an explanatory drawing for the quantity-measuring mechanism and the sample preparation unit of the urine analyzer.

FIG. 6 is a perspective explanatory drawing that shows a quantity-measuring mechanism and a sample preparation unit of the urine analyzer in accordance with the present embodiment, and FIG. 7 is an explanatory drawing thereof. In the present embodiment, a sampling valve 30 is commonly used as the quantity-measuring mechanism that distributes predetermined quantities of the urine specimen to the sample preparation unit (the first sample preparation unit) 2u and the sample preparation unit (the 2nd procurement-of-a-sample part) 2b. This sampling valve 30 consists of two fixed elements having a disc shape, and a movable element pinched by the two fixed elements, and the above-mentioned movable element is operated by a motor 31 so as to pivot.

The sampling valve 30 is provided with two discs 30a and 30b made from alumina ceramics, which are mutually superposed on each other. Channels, used for delivering the sample, are formed in the discs 30a and 30b, and one of the discs 30b rotates around its center shaft as a rotation center so that the channels are divided, and is integrally formed with the sample preparation unit 2b through a fluid cassette 33 which has a channel 32 for samples formed therein. In other words, the sample valve 30, the fluid cassette 33 and the sample preparation unit 2b are placed in a tightly contact state mutually so as to be thermally united; thus, the temperature of the sampling valve 30 is made to be virtually equal to the temperature of the sample preparation unit 2b. On the other hand, the sample preparation unit 2u is fixed to an attachment plate 34 secured to a chassis with bolts 35 with a predetermined clearance S; thus, the sample preparation unit 2u is designed so as to be virtually separated from the sampling valve 30 and the sample preparation unit 2b thermally.

Here, the above-mentioned sample preparation unit 2u and sample preparation unit 2b, which are heated by heaters 36u and 36b which respectively constitute temperature control units, are allowed to adjust the temperature of the sample preparation unit 2u used for preparing the first sample for measuring the particle ingredient in urine that contains at least red corpuscles to a first temperature, and also to adjust the temperature of the sample preparation unit 2b used for preparing the second sample for measuring bacteria to a second temperature higher than the above-mentioned first temperature. More specifically, the sample preparation unit 2u is adjusted to become about 35±2° C., and the sample preparation unit 2b is adjusted to be a higher level, that is, about 42±2° C. As the temperature of the sample becomes higher, it becomes possible to quickly dye predetermined portions (films and cores) of red corpuscles, bacteria and the like, contained in the sample, and consequently to shorten measuring time; however, red corpuscles tend to be easily damaged by high temperatures, and it becomes impossible to carry out accurate measurements when the temperature becomes too high. Therefore, by adjusting the temperature of the second sample used for measuring bacteria having a higher temperature resistance in comparison with particle ingredients in urine so as to become higher than the temperature of the first sample used for measuring the particle ingredients in urine, that is, by adjusting the sample preparation unit 2u and the sample preparation unit 2b to temperatures suitable for the respective measurements, it becomes possible to measure both of the particle ingredients in urine containing red corpuscles and bacterial with high precision. Here, the temperatures of the sample preparation unit 2u and the sample preparation unit 2b can be measured by using, for example, a thermistor. Moreover, the sample preparation unit 2u and the sample preparation unit 2b can be adjusted to temperatures in the above-mentioned predetermined ranges by carrying out on-off control of the above-mentioned heaters 36u and 36b based on the measurement results.

Moreover, by designing the sampling valve 30 and the sample preparation unit 2b to be thermally integral with each other, it becomes possible to prevent the samples temperature-adjusted by the sampling valve 30 from getting cold when supplied to the sample preparation unit 2b, thereby making it possible to reduce the loss of temperature control. Here, in the case of the sample to be supplied to the sample preparation unit 2u that is kept at a temperature lower than that of the sample preparation unit 2b, by allowing the sample channel to pass through the clearance S when the sample is supplied from the sampling valve 30, the temperature can be naturally lowered.

[Determination Criteria According to Medical-Examination Organizations]

In the present embodiment, measurements are carried out on various items of urine in accordance with the following procedures, and the determination criteria on the results of measurement have been stored in the storage unit of the personal computer 13 according to the medical organization, and based upon the determination criteria and actual results of measurements obtained, it is determined whether or not the result of measurements belongs to any of predetermined states, and when, as a result of the determination, the measurement result belongs to any predetermined state, the information indicating this predetermined state is displayed on the display 13a of the personal computer 13. For example, the predetermined state refers to a state in which particle ingredients that do not normally appear in a healthy person's urine appear in a level exceeding the predetermined value, that is, an abnormal state in which the measurement result exceeds a preset limit value with respect to any of measurement items, a state which necessities a recheck based upon mirror check because of appearance of any specific particle ingredient such as columnar cells and epithelial cells, with a specific disease being suspected, or a state in which a possibility of problems with the method for sampling the specimen is raised with the result that a re-sampling of the specimen is required; therefore, upon the determination by the determination means of the CPU 104a of the personal computer 13 that such a state exists, information, such as a comment, a sign and a symbol, indicating the corresponding state is displayed on the display 13a of the personal computer 13 together with numeric values, graphs and the like indicating the results of examination. With this arrangement, a doctor, an inspecting engineer, etc. can carry out the treatment corresponding to the above-mentioned information quickly and appropriately.

With respect to the above-mentioned medical organization, for example, a specialty, a clinic, a hospital, a ward, etc. can be listed, and determination criteria for each of various measurement items are stored according to this medical organization. These determination criteria include reexamination determining conditions used for determining whether the reexamination is required, abnormality determining conditions used for determining whether or not a measurement result is abnormal, and measurement marginal conditions and the like for determining whether it is a sample beyond the performance limit of the analyzer, etc. are included, and these factors can be inputted through a keyboard that is an input means for the personal computer 13, together with the medical organization information identifying the corresponding medical organization; thus, the CPU 104a of the personal computer 13 is provided with a setting means used for storing the inputted determination criteria in its storage unit in a manner so as to be associated with the medical organization information. With this arrangement, the user, such as an inspecting engineer, can set up a determination criteria for every medical organization, and the determination criteria according to each medical organization can be applied easily. Moreover, the above-mentioned CPU 104a is further equipped with an input screen output means that allows the display 13 to output an input screen used for receiving inputs for the medical organization information and determination criteria, and the user is allowed to input necessary information onto the input screen displayed on the display 13a so that the user can set up a determination criteria easily.

Figure 8:
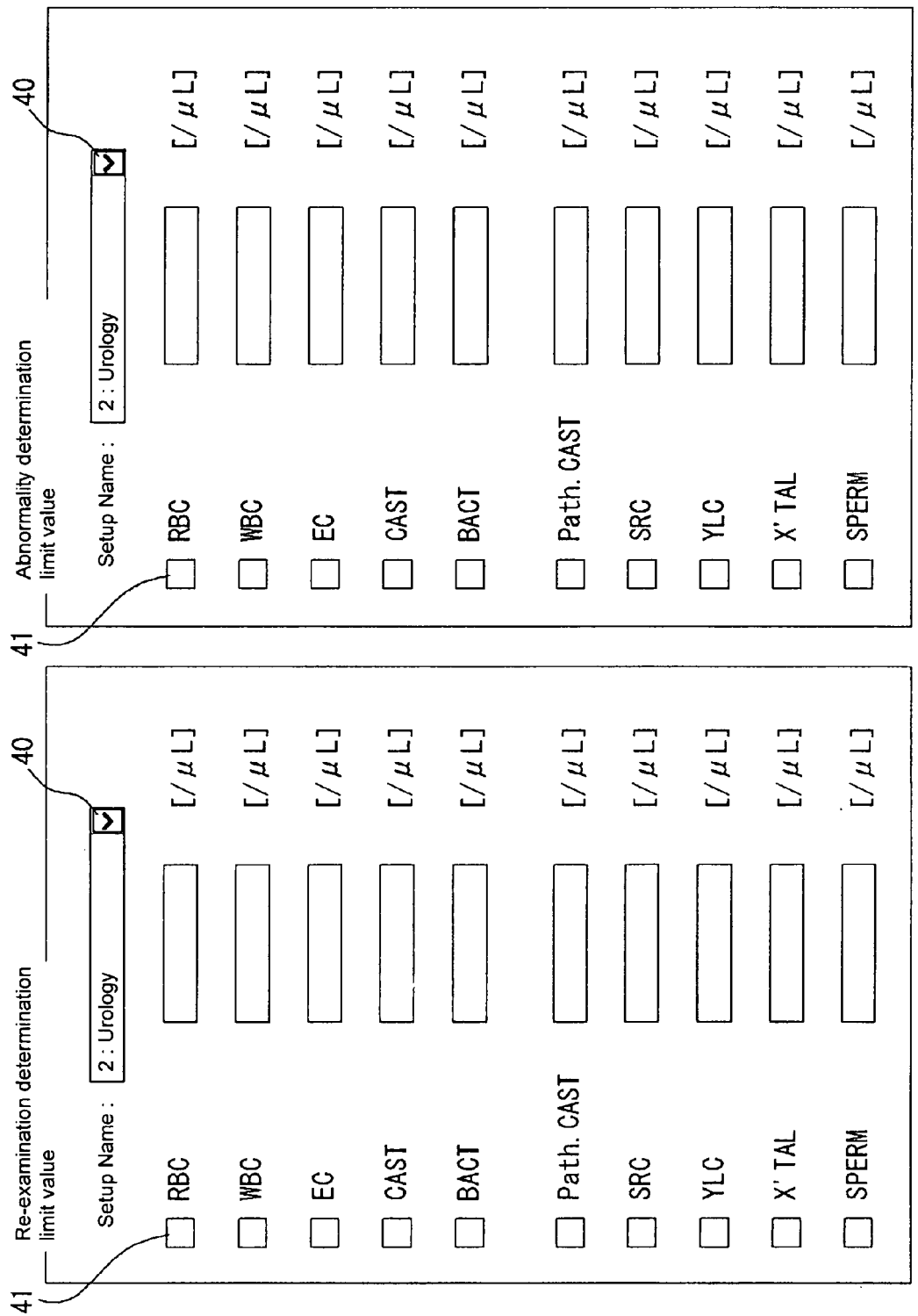
FIG. 8 is a drawing that shows an example of an inputting window for determination criteria.

FIG. 8 is a drawing that shows an example of an input screen for each of the determination criteria used for determining whether or not a measurement result is abnormal (abnormality determination) and whether or not a re-examination (re-examination determination) is required. In FIG. 8, the left-hand side shows a screen which sets up the limit value of the re-examination determination, while the right-hand side shows a screen which sets up the limit value of the abnormality examination. Upon determination of a re-examination as well as upon determination of an abnormality, the user first selects a setup name into which the limited value is to be inputted by clicking a pull down menu 40. This setup name can express the name of determination criteria, and the user can set it up freely with the keyboard 13b which functions as a name input means. Consequently, an easily recognizable name can be set up by this and misrecognition of determination criteria etc. can be prevented. Here, examples of the setup name include: a specialty name, hospital name and ward name by which the medical organization is specified as well as a suspected disease, such as an infection and bloody urine. In the example shown in FIG. 8, a urology department is selected. Moreover, by checking the check boxes 41 on the left-hand side of items to be examined, such as RBC and WBC, selection can be made as to whether a re-examination or a determination on any abnormality should be conducted or not. Thus, with respect to the selected item, limited values that match the respective medical organizations and names of diseases can be set. In this way, the user can set up determination criteria in accordance with the individual medical organizations and diseases. Moreover, since the user can input required information while viewing the screen, it becomes possible to carry out a setup process for the determination criteria easily.

Figure 9:
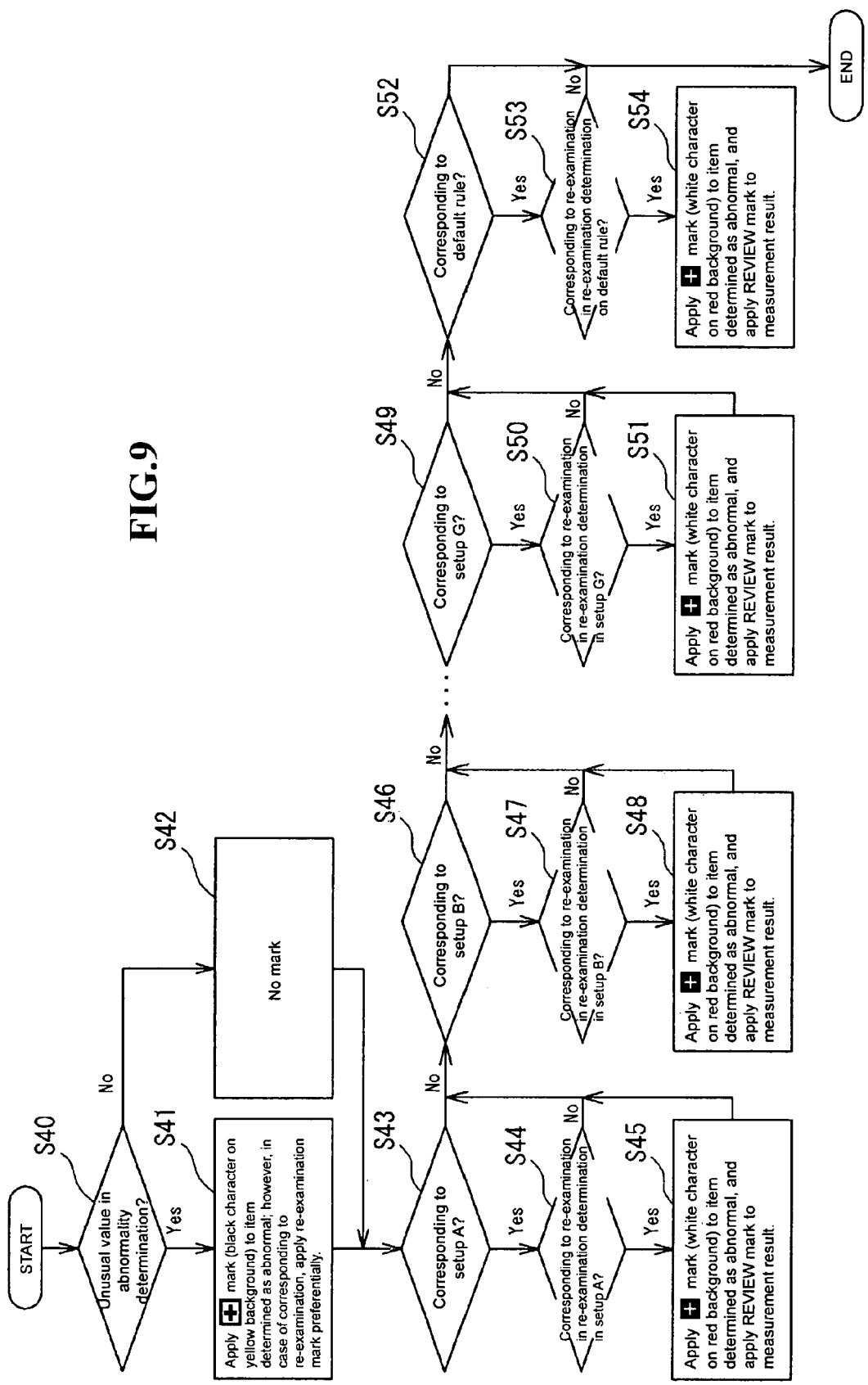
FIG. 9 is a flowchart that shows a procedure of a re-examination determination.

FIG. 9 is a flow chart that shows the procedure of the re-examination in which determination criteria set up as described above are used. When a measurement result is obtained, the CPU 104a first determines whether this measurement result is an abnormal value (Step S40). To an item that has been determined as abnormal, a predetermined mark is attached (Step S41), and when there is no item that has been determined as abnormal, no mark is attached, and a re-examination determination process is successively carried out by the CPU 104a (Step S42).

Figure 10:
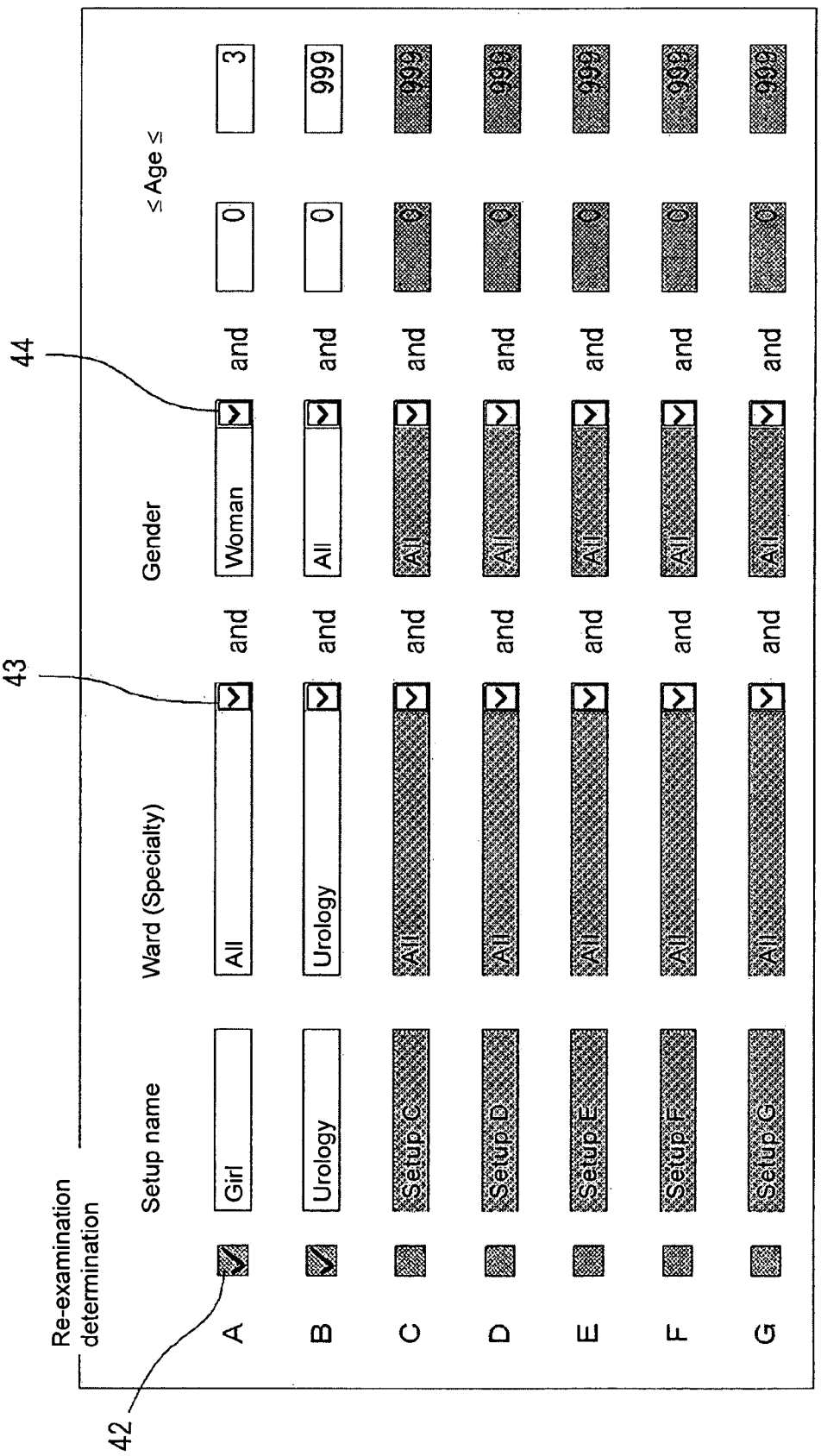
FIG. 10 is a drawing that shows an inputting window for setup conditions used upon carrying out a re-examination determination.

Conditions used for determining the re-examination can also be set up by the user. FIG. 10 is a drawing that explains an input screen used for setup conditions upon carrying out the re-examination determination of FIG. 10. In this example, a maximum of seven conditions can be set up, by checking check boxes 42, selection is made as to whether or not a re-examination determination setup is performed. If a check box 42 is checked, the input of a setup name is allowed so that the user can attach a name freely to each of the conditions. Next, a pull down menu 43 is clicked and a ward (specialty) is selected. This is properly selected from the registered members including the member "All". Next, a pull down menu 44 is clicked and a gender condition is selected from "all", "man" and "woman". Lastly, the minimum and maximum of age conditions are selected.

In accordance with the conditions of the re-examination determination, the determination for the re-examination is made. First, a determination is made as to whether or not a Setup A is satisfied. As will be described later, prior to the examination, a patient's information including the specimen number managed by the host computer, the name, specimen number, age, sex, specialty, etc. of the patient associated with the specimen number, and specimen information, such as measuring items, are preliminarily obtained from the host computer in response to a measuring order inquiry made by an information acquisition means of the personal computer 13. Based upon the specimen information, the CPU 104a determines whether or not the specimen corresponds to Set up A (Step S43), and if so, a determination is made as to whether or not the measurement result corresponds to a re-examination based upon the reexamination determination criteria relating to Setup A (Step S44). Moreover, to an item that has been determined as "re-examination required" by the CPU 104a, a predetermined mark, that is, a "REVIEW" mark which indicates that a re-examination is required, is attached to the measurement result (Step S45). In addition, together with this "REVIEW" mark or in place of this "REVIEW" mark, a comment, such as "a re-examination is required since there are few white corpuscles counts" can also be attached.

In the above-mentioned step S44, after the re-examination determination of Setup A has been completed, regardless of whether or not it corresponds to a re-examination, the determination as to whether or not it corresponds to Setup B is conducted by the CPU 104a, following Setup A (Step S46). When it corresponds, a determination is made as to whether or not the measurement result corresponds to a re-examination based upon the re-examination determination criteria relating to Setup B (Step S47). Moreover, to an item that has been determined as "re-examination required" by the CPU 104a, a predetermined mark, that is, a "REVIEW" mark which indicates that a re-examination is required, is attached to the measurement result (Step S48). In the same manner, the re-examination determination is carried out on each of the setup conditions (Steps S49 to S51).

Next, a determination as to whether or not the measurement result corresponds to any default rule is made by CPU 104a (Step S52), and if it does not correspond, the sequence of operations is completed, and when it corresponds, a default setup is applied so that it is determined whether or not the examination result corresponds to a re-examination based upon the re-examination determination criteria for the corresponding default (Step S53). Moreover, to an item that has been determined as "re-examination required" by the CPU 104a, the "REVIEW" mark which indicates that a re-examination is required is attached to the measurement result (Step S54).

[Analytic Procedure]

Figure 11:
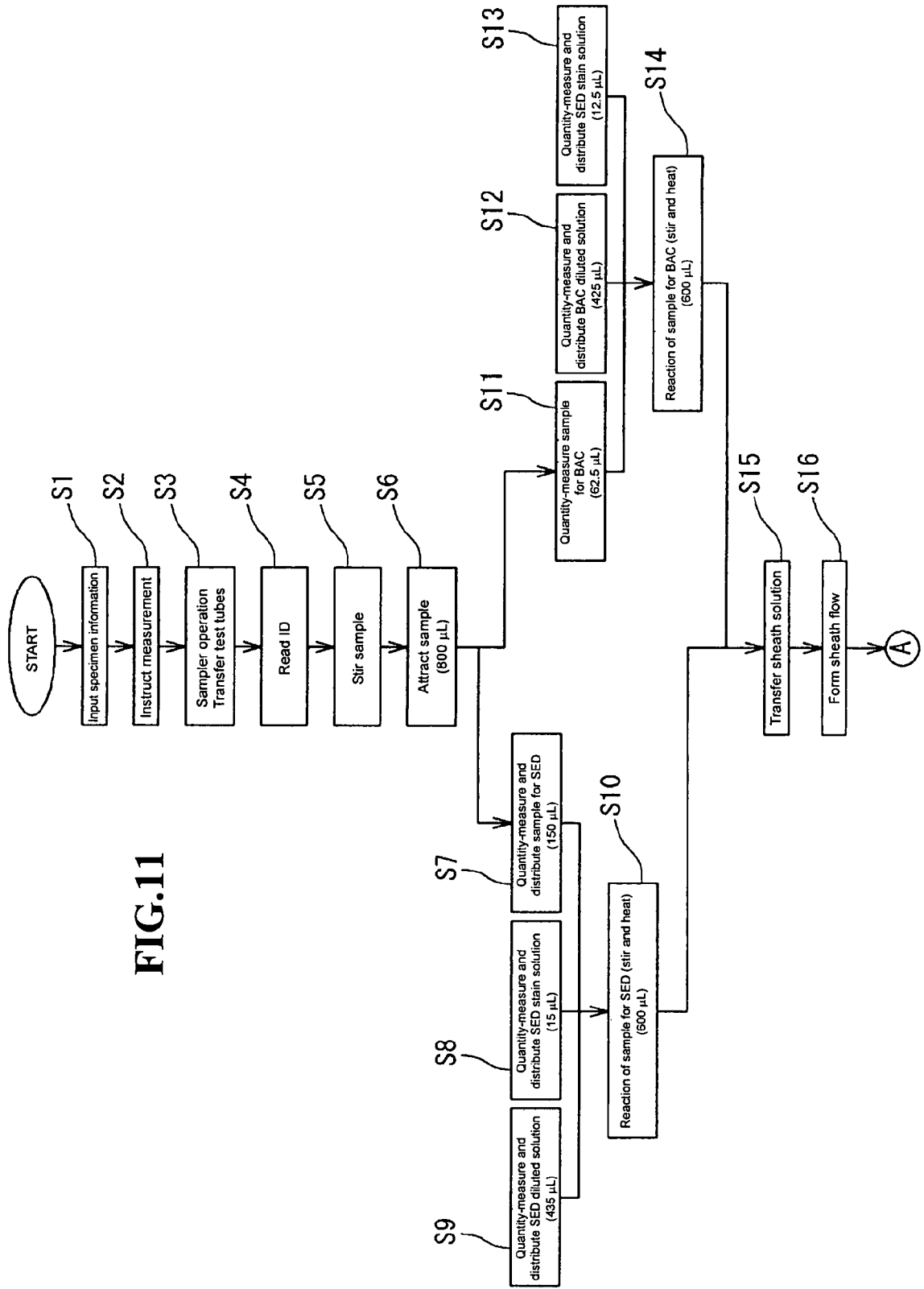
FIG. 11 is a flowchart (first half part) that shows an analytic procedure of urine using the urine analyzer shown in FIG. 1.
Figure 12:
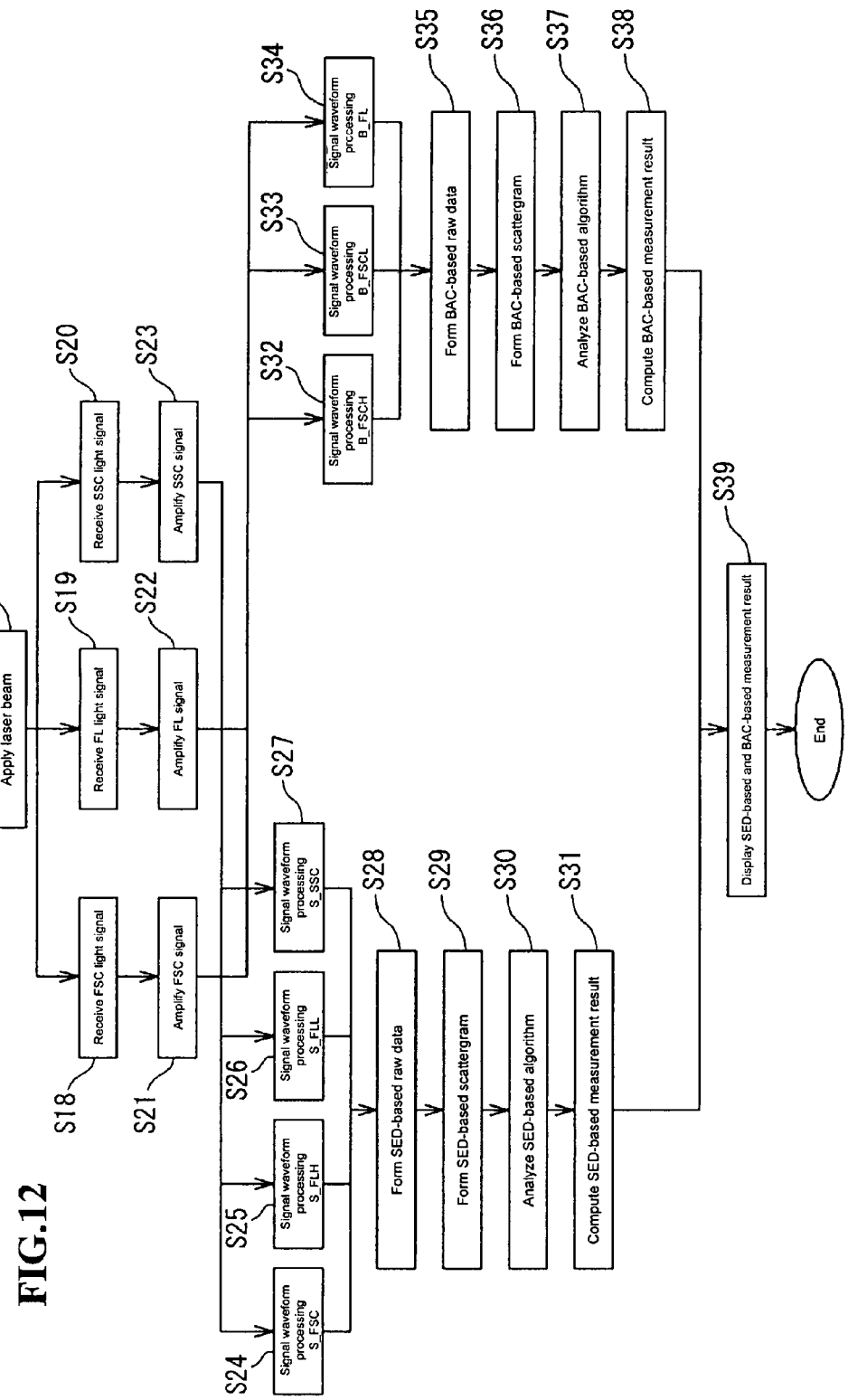
FIG. 12 is a flowchart (second half part) that shows an analytic procedure of urine using the urine analyzer shown in FIG. 1.

Next, according to a flow chart shown in FIGS. 11-12, an analytic procedure for urine, which uses the urine analyzer of the present embodiment including the above-mentioned determination process for the measurement result according to medical organization, is explained.

First, a specimen number managed by the host computer, patient information, including a patient's name, sex, specialty, etc. in association with the corresponding specimen number, and sample information, including a measurement item etc., are preliminarily acquired from the host computer (Step S1). Next, instructions for measurement execution are given by the input device 13b which consists of the keyboard and mouse of the personal computer 13 (Step S2). In response to these instructions, a sample rack 3 on which a test tube T containing a sample is stood is transported to a predetermined suction position by a rack table 4 (Step S3). At this suction position, the above-mentioned test tube T is rotated so that a bar code of ID label stuck onto the peripheral face of the test tube T is read (Step S4). Thus, the specimen number of the sample can be recognized and the measurement item relating to the sample can be specified by comparing the specimen number with the specimen information acquired in Step S1.

Next, a suction pipe 17 is lowered so that the tip portion of the suction pipe 17 is inserted into the sample in the test tube T, and the sample is stirred by repeating suction and discharge of the sample lightly in this state (Step S5). After stirring the sample, a predetermined amount (800 μL) of the sample is sucked and distributed by the sampling valve 30 to the sample preparation unit 2u that prepares a sample used for measuring a particle ingredient containing at least red corpuscles (SED) and the sample preparation unit 2b that prepares a sample used for measuring bacteria contained in urine (BAC), with respective amounts of 150 µL and 62.5 µL (Steps S7 and S11).

To the sample preparation unit 2u, the sample together with predetermined amounts of stain solution (dyeing reagent) and diluting solution are quantity-measured and distributed (Step S8 and Step S9). On the other hand, in the same manner, to the sample preparation unit 2b, the sample together with predetermined amounts of stain solution (dyeing reagent) and diluting solution are quantity-measured and distributed (Step S12 and Step S13). The sample preparation unit 2u and the sample preparation unit 2b are warmed to predetermined temperatures by heaters 36u and 36b respectively, and in this state, these are subjected to sample stirring processes by propeller-like stirring tools (not shown)(Step S10 and Step S14). In addition, a surface-active agent is contained in the diluting solution to be distributed to the sample preparation unit 2u in Step S9, and damages are subsequently given to a bacteria film so that it becomes possible to dye a bacterial core efficiently.

Subsequently, sheath liquid is transported to a sheath flow cell 51 of the optical detecting unit 5 (Step S15) and thereafter, first, the sample used for measuring the particle ingredient in urine (SED) is led to the optical detecting unit 5 in which a narrow flow (sheath flow) wrapped with the sheath liquid is formed in the sheath flow cell 51 (Step S16). The sheath flow thus formed is irradiated with a laser beam from a semiconductor laser 53 (Step S17). The reason that the measurement for the particle ingredient in urine is preliminarily carried out is because, when, after measuring the bacteria, the measurement for the particle ingredient in urine is carried out, the surface-active agent, contained in the sample used for the bacteria measurement, is mixed into the sample used for measuring the particle ingredient in urine due to the carryover of the sample to cause damages to the film of the particle ingredient in urine containing red corpuscles, with the result that the measurement for the particle ingredient in urine tends to be adversely affected.

Forward scattering light, fluorescence and side scattering light of the particle ingredient, generated by the irradiation with the laser beam, are respectively received by a photo-diode 55, a photo-multiplier 59 and a photo-multiplier 58 and converted to electric signals, and are then outputted as a forward scattering light signal (FSC), a fluorescence signal (FL) and a side scattering light signal (SSC)(Steps S18 to S20). These outputs are amplified by pre-amplifiers (Steps S21 to S23).

Upon completion of the measurement on the sample used for measuring the particle ingredient in urine (SED), the bacteria in urine are successively measured by using the sample prepared in Step S14. In this case, a forward scattering signal (FSC) and a fluorescent signal (FL) are outputted in the same manner as those in the aforementioned Steps S15 to 23 by the optical detecting unit 5 used in the measurement for the particle ingredient in urine, and then amplified.

The amplified forward scattering light signal (FSC), fluorescence signal (FL) and side scattering light signal (SSC) are converted to digital signals in the signal processing circuit 10 (see FIG. 7), and also subjected to predetermined waveform treatments (Steps S24 to S27), and the resulting signals are sent to the personal computer 13 through an LAN adaptor 12. Here, "FLH" in step S25 refers to a signal obtained by amplifying the fluorescence signal (FL) by using a high gain, and "FLL" in step S26 also refers to a signal obtained by amplifying the fluorescence signal (FL) by using a low gain.

Moreover, raw data relating to the particle ingredient in urine (SED) are formed in the personal computer 13 (Step S28), and based upon these data, a scattergram is formed (Step S29). Next, a clustering process is carried out on the scattergram thus formed through an algorithm analysis by the CPU 104a (Step S30), and the number of particles is counted for each of the clusters (Step S31).

Furthermore, in the same manner, with respect to the bacteria, the forward scattering signal (FSC) and fluorescence signal (FL), which have been amplified, are converted to digital signals and then subjected to predetermined waveform treatments in the signal processing circuit 10 (Steps S32 to S34). Here, "FSCH" in step S32 refers to a signal obtained by amplifying the forward scattering light signal (FSC) by using a high gain, and "FSCL" in step S33 also refers to a signal obtained by amplifying the fluorescence signal (FSC) by using a low gain.

The resulting signals are then sent to the personal computer 13 through a LAN adopter 12. Moreover, raw data relating to the bacteria (BAC) are formed in the personal computer 13 (Step S35), and based upon these data, a scattergram is formed (Step S36). Next, a clustering process is carried out on the scattergram thus formed through an algorithm analysis by the CPU 104a (Step S37), and the number of particles is counted for each of the clusters (Step S38). Each of the measurement results thus obtained is determined as to whether or not a re-examination is required or whether or not there is any abnormality contained based upon the determination criteria according to the clinical organization, and is then displayed on the display 13a serving as the display means of the personal computer 13 together with the determination result, the corresponding comment and the like (Step S39).

Additionally, the present embodiment has explained the structure in which the measurement result is compared with each of the determination criteria according to clinical organizations registered, and the determination is made as to whether or not a re-examination is required or whether or not there is any abnormality contained for each of the specialties registered; however, not limited to this structure, for example, another structure may be adopted in which: an input from a specialty relating to a patient is received by the personal computer 13 through a manual input by the user or by data received from the host computer, and by comparing the measurement result with the inputted determination criteria of the specialty, a determination is made as to whether or not a re-examination is required or whether or not there is any abnormality contained, with respect to the inputted specialty. With this arrangement, only the determination result relating to the specialty for the patient can be outputted so that only the necessary information is supplied to the user.

As described above, the urine analyzer U makes it possible to determine whether or not a measurement result corresponds to a predetermined state by using determination criteria prepared for each of medical organizations (for example, a specialty, a hospital, a hospital, a ward, etc.). With this arrangement, it becomes possible to carry out a precise, detailed determination by taking into consideration the individual situation of each medical organization, and consequently to eliminate the necessity of a doctor etc. having to carrying out a re-determination, which makes the present system different from the prior art.

Additionally, the above-mentioned embodiment has explained a system in which a urine analyzer is prepared as the clinical examination apparatus; however, not limited to this structure, for example, another clinical examination apparatus, such as a blood cell counting device, a blood coagulation measuring device, an immunity analyzer and a biochemical analyzer, may be used.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A urine specimen measuring apparatus located in a medical facility, the apparatus comprising:
   a suction pipe having a tip end configured to insert into a test tube containing a urine specimen obtained from a patient, wherein the suction pipe inserted into the test tube is controlled to repeatedly suction and discharge the urine specimen, thereby stirring the urine specimen in the test tube, the suction pipe is further controlled to aspirate an initial portion of the stirred urine specimen and to distribute the aspirated initial portion of the urine sample into a first aliquot and a second aliquot;
   a first measurement sample preparation unit configured to contain a first measurement sample that includes a first dyeing reagent and the first aliquot and is used for counting erythrocytes;
   a second measurement sample preparation unit configured to contain a second measurement sample that includes a second dyeing reagent and the second aliquot and is used for counting bacteria;
   an optical detecting unit comprising a sheath flow cell configured to form a first flow of the first measurement sample and a second flow of the second measurement sample, a semiconductor laser light source configured to irradiate the first and second flows, a scattered light detector configured to detect first scattered light information from particles in the first flow and to detect second scattered light information from particles in the second flow and a fluorescence detector configured to detect first fluorescence information from the particles in the first flow and to detect second fluorescence information from the particles in the second flow;
   a memory configured to store a first re-examination determination condition including gender, age range and first determination criteria of the number of erythrocytes and the number of bacteria, and a second re-examination determination condition including gender, age range and second determination criteria of the number of erythrocytes and the number of bacteria;
   a specimen information acquirer configured to acquire specimen information for the urine specimen;
   a receiver configured to receive patient information indicating gender and age of a patient of the urine specimen and medical specialty information identifying the first and second branch of medical science;
   a display; and
   a computer configured to determine whether or not a first re-examination for a first branch of medical science is required for a urine specimen, and to determine whether or not a second re-examination for a second branch of medical science is required for the urine specimen by performing operations comprising:
   acquiring the specimen information for the urine specimen,
   receiving the patient information and the medical specialty information identifying at least one of the first and second branch of medical science on the basis of the specimen information,
   preparing a measurement result including at least the number of the erythrocytes and the number of the bacteria from the detected first and second scattered light information by the scattered light detector and the detected first and second fluorescence information by the fluorescence detector;
   responsive to receiving the medical specialty information of the first branch of medical science, determining whether or not the first re-examination is required by comparing the measurement result, the gender of the patient and the age of the patient to the first re-examination determination condition of the medical specialty information of the first branch of medical science;
   displaying first re-examination information on the display, when the first re-examination is required, the first re-examination information indicating that the first re-examination is required;
   responsive to receiving the medical specialty information of the second branch of medical science, determining whether or not the second re-examination is required by comparing the measurement result, the gender of the patient and the age of the patient to the second re-examination determination condition of the medical specialty information of the second branch of medical science; and
   displaying second re-examination information on the display, when the second re-examination is required, the second re-examination information indicating that the second re-examination is required.

2. The urine specimen measuring apparatus according to claim 1, wherein the specimen information included a specimen number.

3. The urine specimen measuring apparatus according to claim 1,
   wherein the memory stores a first abnormality determination condition determining whether or not the measurement result is in a first abnormal state and a second abnormality determination condition determining whether or not the measurement result is in a second abnormal state,
   wherein the computer performs operations comprising:
   determining whether or not the measurement result is in the first abnormal state by comparing the measurement result to the first abnormality determination condition when the acquired medical specialty information include the first branch of medical science, and displaying first abnormal information indicating that the measurement result is in the first abnormal state on the display, when the measurement result is in the first abnormal state,
   wherein the computer performs operations comprising:
   determining whether or not the measurement result is in the second abnormal state by comparing the measurement result to the second abnormality determination condition when the acquired medical specialty information include the second branch of medical science, and displaying second abnormal information indicating that the measurement result is in the second abnormal state on the display unit, when the measurement result is in the second abnormal state.

4. The urine specimen measuring apparatus according to claim 1, wherein the computer performs operations further comprising:
receiving an input of medical specialty information and re-examination determination condition, the medical specialty information specifying a medical organization; and
storing the input re-examination determination condition in the memory in association with the medical specialty information.

5. The urine specimen measuring apparatus according to claim 4, wherein the computer performs operations further comprising displaying an input screen on the display for receiving the input of the medical specialty information and the re-examination determination condition.

6. The urine specimen measuring apparatus according to claim 4, wherein the computer performs operations further comprising:
receiving an input of a name of the re-examination determination condition, and
storing the inputted name in the storage unit in association with the re-examination determination condition.

7. A urine specimen measuring apparatus located in a medical facility, the apparatus comprising:
a suction pipe having a tip end configured to insert into a test tube containing a urine specimen obtained from a patient, wherein the suction pipe inserted into the test tube is controlled to repeatedly suction and discharge the urine specimen, thereby stirring the urine specimen in the test tube, the suction pipe is further controlled to aspirate an initial portion of the stirred urine specimen and to distribute the aspirated initial portion of the urine sample into a first aliquot and a second aliquot;
a first measurement sample preparation unit that contains a first measurement sample that includes a first dyeing reagent and the first aliquot and is used for counting erythrocytes;
a second measurement sample preparation unit configured to contain a second measurement sample that includes a second dyeing reagent and the second aliquot and is used for counting bacteria;
an optical detecting unit comprising a sheath flow cell configured to form a first flow of the first measurement sample and a second flow of the second measurement sample, a semiconductor laser light source configured to irradiate the first and second flows, a scattered light detector configured to detect first scattered light information from particles in the first flow and to detect second scattered light information from particles in the second flow and a fluorescence detector configured to detect first fluorescence information from the particles in the first flow and to detect second fluorescence information from the particles in the second flow;
a display;
a memory that stores a plurality of urine re-examination determination conditions, wherein each of the re-examination determination conditions is applied by each branch of medical science of the medical facility, includes gender, age range and determination criteria of the number of erythrocytes and the number of bacteria, and determines whether or not a re-examination of a urine specimen for each of the branches of medical science is required;
a receiver for receiving patient information including gender and age of a patient of the urine specimen and medical specialty information identifying at least one of the branches of medical science;
a computer configured to perform operations comprising:
receiving the patient information and the medical specialty information identifying at least one of the branches of medical science on the basis of the urine specimen obtained from the patient,
preparing a measurement result including at least the number of the erythrocytes and the number of the bacteria from the detected first and second scattered light information and the detected first and second fluorescence information from the first and second measurement samples;
determining whether or not the re-examination is required by comparing the measurement result, the gender of the patient and the age of the patient to the re-examination determination condition applied by the at least one branch of medical science; and
displaying re-examination information indicating that the re-examination is required when it is determined that the re-examination is required.

8. The urine specimen measuring apparatus according to claim 7, wherein the receiver comprises an input device that receives medical specialty information and the re-examination determination condition; and
the computer stores the inputted re-examination determination condition in the memory in association with the medical specialty information.

9. The urine specimen measuring apparatus according to claim 8, wherein the computer performs operations further comprising displaying an input screen that receives the input of the medical specialty information and the re-examination determination condition on the display.

10. The urine specimen measuring apparatus according to claim 8, wherein the receiver is configured for receiving an input of a name of the patient, and the computer stores the inputted name in the memory in association with the re-examination determination condition.

11. A urine examination method performed by a urine specimen measuring apparatus located in a medical facility, the method comprising:
stirring a urine specimen obtained from a patient in a test tube by repeating suction and discharge of the urine specimen by a suction pipe inserted into the test tube;
aspirating an initial portion of the stirred urine specimen by the suction pipe;
distributing the initial portion of the aspirated urine specimen into a first aliquot and a second aliquot;
preparing a first measurement sample for counting erythrocytes from a first dyeing reagent and the first aliquot;
preparing a second measurement sample for counting bacteria from a second dyeing reagent and the second aliquot;
subjecting the first measurement sample to an optical detection unit comprising a sheath flow cell, a semiconductor laser light source, a scattered light detector and a fluorescence detector and detecting first scattered light information from particles in the first measurement sample by the scattered light detector and first fluorescence information from particles in the first measurement sample by the fluorescence detector;
subjecting the second measurement sample to the optical detection unit and detecting second scattered light information from particles in the second measurement sample by the scattered light detector and second fluorescence information from particles in the second measurement sample by the fluorescence detector;

using a computer in electronic communication with the urine specimen measuring apparatus to carry out the following operations: receiving patient information indicating gender and age of a patient of the urine specimen and medical specialty information identifying at least one of a plurality of branches of medical science;

preparing a measurement result including at least the number of the erythrocytes and the number of the bacteria from the detected first and second scattered light information and the detected first and second fluorescence information;

receiving a urine re-examination determination condition including gender, age range and determination criteria of the number of erythrocytes and the number of bacteria, and applied by the at least one branch of medical science for a urine specimen from a memory that stores a plurality of re-examination determination conditions applied by each branch of medical science of the medical facility to evaluate measurement results;

determining whether or not the re-examination is required by comparing the measurement result, the gender of the patient and the age of the patient with the received re-examination determination condition applied by the at least one branch of medical science; and displaying re-examination information indicating that the re-examination is required on a display, when it is determined that the re-examination is required.

12. The urine examination method according to claim 11, wherein the memory stores a plurality of abnormality determination conditions, each of the abnormality determination conditions determining whether or not the measurement result is in an abnormal state, wherein comparing the measurement result with the re-examination determination condition further comprises comparing the measurement result with the abnormality determination condition, the step of determining whether or not the re-examination is required further comprises determining whether or not the measurement result is in the abnormal state from the comparing result of the measurement result and the abnormality determination condition, and displaying information further comprises displaying the abnormal information on the display.

13. The urine examination method according to claim 11, further comprising:

receiving an input of medical specialty information and re-examination determination condition, the medical specialty information identifying a branch of medical science and the re-examination determination condition assigned by the medical specialty; and storing the input re-examination determination condition in the memory in association with the medical specialty information.

\* \* \* \* \*